United States Patent [19]

Falk et al.

[11] Patent Number: 4,636,150

[45] Date of Patent: Jan. 13, 1987

[54] LOW POWER ELECTROMAGNETIC PUMP

[75] Inventors: Theodore J. Falk, Clarence; Lawrence E. Morris, Bowmansville, both of N.Y.

[73] Assignee: Greatbatch Enterprises, Inc., Clarence, N.Y.

[21] Appl. No.: 617,486

[22] Filed: Jun. 5, 1984

Related U.S. Application Data

[63] Continuation-in-part of Ser. No. 496,822, May 23, 1983, Pat. No. 4,568,250, which is a continuation-in-part of Ser. No. 415,657, Sep. 7, 1982, Pat. No. 4,569,641.

[51] Int. Cl.$^4$ .................................. F04B 17/04
[52] U.S. Cl. .................................. 417/417; 417/444; 417/505; 310/104
[58] Field of Search ............... 417/417, 416, 505, 486, 417/487, 444, 445; 310/32, 30, 28, 89, 104; 128/DIG. 12; 604/123, 152

[56] References Cited

U.S. PATENT DOCUMENTS

| | | | |
|---|---|---|---|
| 1,590,868 | 6/1926 | Wallace | 417/417 |
| 2,533,164 | 12/1950 | Dickey et al. | 417/417 |
| 2,681,695 | 6/1954 | Bills et al. | 417/417 |
| 2,951,447 | 9/1960 | Casassa | 310/104 |
| 3,601,509 | 8/1971 | Kreitchman | 417/417 |
| 4,269,572 | 5/1981 | Nozawa et al. | 417/417 |

*Primary Examiner*—Carlton R. Croyle
*Assistant Examiner*—Donald E. Stout
*Attorney, Agent, or Firm*—Christel, Bean & Linihan

[57] ABSTRACT

An electromagnetic pump comprising a housing having a fluid receiving chamber in communication with an inlet, a pair of fluid chambers connected by a fluid by-pass passage to accommodate bubbles, one in communication with the fluid receiving chamber and the other in communication with an outlet, an electromagnet carried by the housing located external to the fluid chambers thereof, and a barrier in the form of a thin diaphragm of fluid impermeable material which hermetically isolates the electromagnet from the fluid chambers. An armature in the housing is movable within a body of magnetically permeable material which contains the bypass, has a pole portion located for magnetic attraction by the electromagnet, and has a piston portion, preferably of smaller cross-section than the pole portion, for forcing fluid from the fluid chambers and through the outlet. The armature is moved from a rest position through a forward pumping stroke when attracted by the electromagnet and is moved by a biasing spring in an opposite direction through a return stroke back to the rest position. A main valve is movably carried by the armature and located in the fluid receiving chamber for closing the pump inlet when the armature is in the rest position and allowing opening the inlet after the armature begins the forward pumping stroke. The structure and arrangement of the check valve minimizes the volume of the fluid receiving chamber to limit the maximum size of a bubble contained therein. A bypass passage containing a check valve which opens during the armature return stroke provides a path for bubbles around the piston to the fluid receiving chamber.

20 Claims, 9 Drawing Figures

LOW POWER ELECTROMAGNETIC PUMP

CROSS REFERENCE TO RELATED APPLICATIONS

This application is a continuation-in-part of our pending U.S. Pat. application Ser. No. 496,822 filed May 23, 1983, now Pat. No. 4,568,250, and entitled "Low Power Electromagnetic Pump" which is a continuation-in-part of pending U.S. Pat. application Ser. No. 415,657 filed Sept. 7, 1982, now Pat. No. 4,569,641, and entitled "Low Power Electromagnetic Pump".

BACKGROUND OF THE INVENTION

This invention relates to the art of electromagnetically operated fluid pumps and more particularly to a new and improved electromagnetic pump which operates at extremely low power.

One area of use of the present invention is implantable drug delivery systems, although the principles of the present invention can be variously applied. The principal requirements for a pump in such applications are low power drain, since the pump must be driven by an implanted battery, and compatibility with the drug being pumped. Another important requirement is that the pump be capable of operating with bubbles present in the liquid being pumped. In addition, there is the desirability of achieving increased maximum available pumping rate, some relaxation of tolerances between certain parts of the pump, pumping against higher back pressures without saturating the pump magnetic circuit, and improved stability of stroke volume.

It would therefore, be highly desirable to provide an electromagnetically-operated pump which is safe, reliable, small in size, light in weight which operates without excessive demand on the available energy supply, which is compatible with drugs or similar liquids to be pumped, which is capable of operating with bubbles present in the liquid being pumped, which has an increased maximum available pumping rate, wherein tolerances between some of the parts thereof are relaxed, which pumps against higher back pressure without saturating the pump magnetic circuit, and which has an improved stability of stroke volume.

SUMMARY OF THE INVENTION

It is, therefore, a primary object of this invention to provide a new and improved electromagnetically-operated pump.

It is a more particular object of this invention to provide such a pump which operates at extremely low power levels It is a further object of this invention to provide such a pump which is electrically and magnetically efficient.

It is a further object of this invention to provide such a pump which is capable of operating with bubbles present in the liquid being pumped.

It is a further object of this invention to provide such a pump which has an increased maximum available pumping rate.

It is a further object of this invention to provide such a pump wherein tolerances between some of the parts thereof are relaxed. It is a further object of this invention to provide such a pump which pumps against higher back pressure without saturating the pump magnetic circuit.

It is a further object of this invention to provide such a pump which has an improved stability of stroke volume.

It is a more particular object of this invention to provide such a pump which is small in size, light in weight and reliable in operation.

The present invention provides an electromagnet pump comprising a housing having a fluid receiving chamber in communication with an inlet, a first fluid pumping chamber in fluid communication with the receiving chamber, a second fluid chamber in fluid communication with an outlet, electromagnet means carried by the housing located external to the fluid chambers thereof, and barrier means in the form of a thin diaphragm of fluid impermeable material which hermetically isolates the electromagnet from the fluid chambers. An armature in the housing is closely fitted and movable within a body of magnetically permeable material located in the housing between the first and second fluid chambers, and the armature has a pole portion located for magnetic attraction by the electromagent means. The armature also has a plunger portion located in the first pumping chamber nas the pole portion located in the second fluid chamber, and has a piston portion to force fluid out of the chambers and through the pump outlet. The armature piston portion is movably supported in the pump housing and located on the inlet side of the armature plunger. A bypass passage is defined through the body in direct communication with the first and second fluid chambers to allow bubbles in the fluid to pass the body and armature pole portion with little pressure drop. The bypass passage also accommodates an armature piston smaller in cross-section than the armature pole portion. The armature is moved from a rest position through a forward pumping stroke when attracted by the electromagnet means to force fluid from the first pumping chamber to the second fluid chamber and then out of the second chamber through the outlet, and the armature is moved by biasing means in an opposite direction through a return stroke back to the rest position. A magnetic circuit is defined including the electromagnet means, a portion of the fluid-impermeable barrier, the body, the armature pole portion, and a gap defined between the pole portion and the electromagnet which gap is closed during movement of the armature toward the electromagnet during energization thereof.

The pump is made electrically and magnetically efficient by minimizing the total gap within the magnetic circuit, by having the pole face area relatively large on the armature pole portion, and by having the electromagnet include a coil on a core of relatively small diameter. A pump check valve is within the pump and associated with the armature in the form of a valve member located inthe fluid receiving chamber, movably carried by the armature and biased by a conical spring between the armature and valve member, and positioned for closing the pump inlet when the armature is in the rest position and for allowing opening of the inlet after the armature begins the forward pumping stroke. The arrangement and structure of the valve member and provision of the conical spring minimizes the internal volume of the pump thereby limiting the maximum size of a bubble which can be contained therein. The armature piston is closely fitted and movable within the pump body, and there is provided a bypass passage in the pump body between the first pumping chamber and the fluid receiving chamber to provide a path around the piston for bubbles. Check valve means in the passage opens during the return stroke of the piston. The piston diameter can be reduced to allow pumping against higher back pressures without saturating the magnetic circuit, to improve the stability of stroke volume and to reduce the internal volume of the pump.

The foregoing and additional advantages and characterizing features of the present invention will become clearly apparent upon a reading of the ensuing detailed description together with the included drawing wherein:

BRIEF DESCRIPTION OF THE DRAWING FIGURES

DETAILED DESCRIPTION OF THE ILLUSTRATED EMBODIMENT

Figure 2:
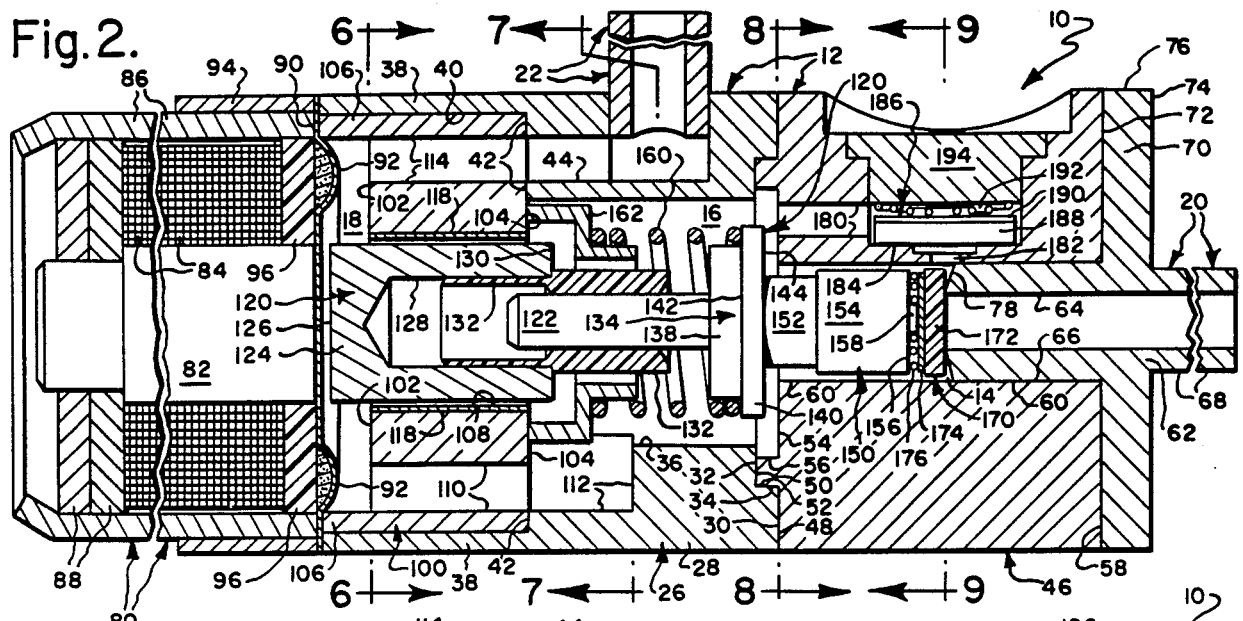
FIG. 2 is an enlarged longitudinal sectional view of the pump of FIG. 1 showing the armature in a rest postion with the main check valve in a closed position and the bypass check valve in a closed position.
Figure 3:
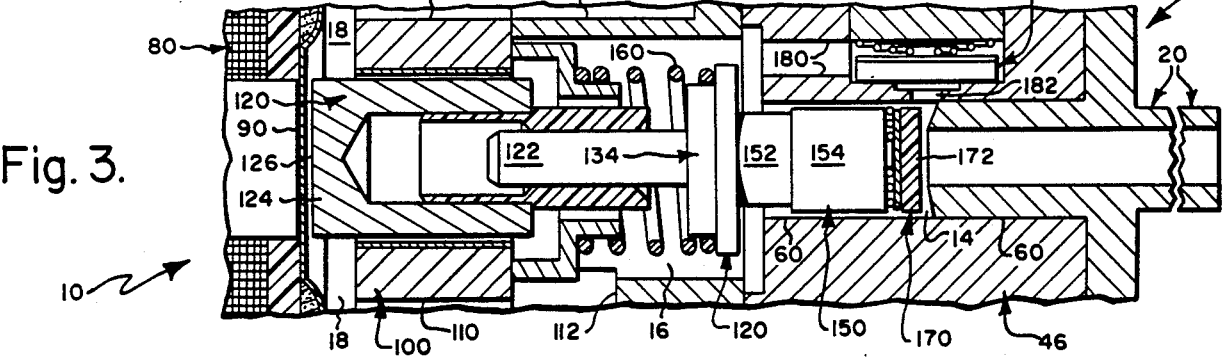
FIG. 3 is a fragmentary longitudinal sectional view of the pump of FIG. 2 showing the armature in an energized position and the main check valve in an open position and the bypass check valve in a closed position.

Referring now to FIGS. 1-5, a pump 10 according to the present invention includes a housing 12 which is generally hollow cylindrical in overall shape and includes an interior region for containing fluid, i.e. the liquid to be pumped. As shown in FIG. 2, the hollow interior region is divided in a manner which will be described into a fluid receiving chamber 14, a first fluid pumping chamber 16 in fluid communication with receiving chamber 14, and a second fluid chamber 18 in fluid communication with pumping chamber 16. There is an inlet generally designated 20 in fluid communication with the receiving chamber 14 and adapted to be connected to a source or supply of fluid to be pumped. There is also an outlet 22 in fluid communication with the second fluid chamber 18 and adapted to be in fluid communication with a location to which the fluid is to be pumped. There is provided check valve means operatively associated with the fluid containing region of pump 10 for allowing fluid flow in a direction from the inlet 20 through outlet 22 and blocking fluid flow in a direction from the outlet through the inlet. In the pump shown the check valve is within the pump and associated with the pump armature in a manner which will be described.

Referring now to FIG. 2, housing 12 is generally hollow cylindrical in overall shape including a central body portion 26 including a section 28 of substantial wall thickness. Section 28 terminates at the right-hand end as viewed in FIG. 2 in axially offset annular end faces 30 and 32 which meet in an annular shoulder 34 for a purpose to be described. Section 28 has an interior surface 36 of constant diameter. Body portion 26 also includes a section 38 extending axially from the opposite end of section 28, i.e. to the left as viewed in FIG. 2, which is of relatively smaller wall thickness. End section 38 has a relatively larger diameter inner wall surface 40 which meets surface 36 in annular intermediate wall 42.

Central body portion 26 is provided with a bore or passage 44 extending parallel to the pump longitudinal axis offset therefrom for placing the second fluid chamber 18 in fluid communication with outlet 22. Outlet 22 is located on the side of housing 12 for communication with the passage 44. Housing section 28 is provided with a radially extending opening in the outer wall thereof in communication with passage 44.

A housing extension portion 46 is provided between central body portion 26 and inlet 20. Portion 46 is generally cylindrical, having an outer diameter substantially equal to the outer diameter of central portion 26 whereby the outer surfaces thereof are substantially flush. Portion 46 abuts portion 26, in particular section 28, and includes at the end facing section 28 an outer annular end face 48 and an intermediate annular end face 50 which meet in an annular shoulder 52. End faces 28 and 50 together with shoulder 52 conform to end faces 30 and 32 together with shoulder 34 of section 28 in a close-fitting, mating relationship as shown in FIG. 2. Portions 26 and 46 are secured together by welding or other suitable means. Portion 46 also has a central axial end face 54 offset axially inwardly from end face 50 thereby defining another annular shoulder 56. The opposite end of portion 46, i.e. the right hand end as viewed in FIG. 2, terminates in a planar axial end face 58. Portion 46 is provided with a central longitudinal bore or passage 60 of constant diameter extending the entire axial length of portion 46 between end faces 54 and 58.

Inlet 20 is provided by a plug-like element in the form of a tube or cylinder 62 having an interior surface 64 of constant diameter and outer surface portions 66 and 68 separated by a radially outwardly extending annular rim or flange 70 having oppositely disposed annular axial end faces 72 and 74 which meet in an annular outer surface 76. The element is fitted into the open end of housing portion 46 with the outer diameter of surface 66 being substantially equal to the diameter of passage 60 thereby providing a close fit therein. The one end of the fitting is a beveled or angularly disposed end face 78 which is located approximately mid-way along the length of passage 60. Surfaces 78 and 64 meet in a sharp annular edge End face 72 of flange 70 contacts end face 58 of housing portion 46 and the outer surface 76 is of substantially the same diameter as portion 46 so that the outer surfaces are substantially flush. The two components are secured together by welding or other suitable means. Inlet 20 is adapted for connection to a conduit such as a flexible tubing leading from a source or supply of fluid to be pumped.

By way of example, in an illustrative pump, housing 12 including central body portion 26 and extension portion 46, together with inlet and outlet fittings 20 and 22, respectively, all are of metal, and for a drug delivery pump for implantation in a patient, titanium has been found to provide satisfactory results. In such an illustrative pump, housing 12 has an outer diameter of about 0.280 inch and overall length of about 0.5 inch measured between the axial end face of section 38 and end face 58. The housing central body portion has an axial length of about 0.290 inch. Surface 36 has a diameter of about 0.15 inch and shoulder 24 has a diameter of about 0.200 inch. Surface 40 has a diameter of about 0.26 inch, and the axial end face of housing section 38 has a radial thickness of about 0.02 inch. Passage 44 in the housing body 26 and the interior passage in outlet fitting 22 both have a diameter of about 0.029 inch. The housing extension portion 46 has an axial length of about 0.204 inch. End face 54 has a diameter of about 0.200 inch, and passage 60 has a diameter of about 0.070 inch. In the inlet plug fitting 20, passage 64 has a diameter of about 0.036 inch, surface 66 has a diameter of about 0.069 inch, surface 68 has a diameter of about 0.062 inch, flange 70 has a thickness of about 0.030 inch, surface 76 has a diameter of about 0.280 inch, the overall axial length of the fitting is 0.244 inch, and surface 78 is disposed at an angle of about 15° with respect to a plane perpendicular to the fitting longitudinal axis.

The pump of the present invention further comprises electromagnet means generally designated 80 carried by housing 12 and located external to the fluid containing region of the housing. As shown in FIG. 2, the electromagent includes a core 82 in the form of a spool which is generally solid cylindrical in shape. A coil 84 is wound on spool 82 and contained within a hollow housing 86 generally cylindrical in shape. One end of electromagnet 80 is adjacent and in abutting relation to housing 12, and the opposite end, i.e. the left-hand end as viewed in FIG. 2, is closed by suitable means, such as a pair of metal washers 88 fitted within the open end of housing 86 and fitted onto an end of spool 82. Electromagnet 80 is joined to housing 12 in the following manner.

The interior, fluid containing region of housing 12 and the electromagnet are separated by a barrier means of fluid impervious material in the form of a relatively thin plate or diaphragm-like component 90. Plate 90 is provided with an annular strengthening rib 92. The end of magent housing 86 adjacent housing 12 is provided with an annular band 94 around the outer surface and adjacent the axial end face of housing 86. The outer diameter of band 94 when placed on housing 86 is substantailly equal to the outer diameter of housing section 38 so that the respective outer surfaces are substantailly flush. The axial end faces of band 94 and magnet housing 86 are coplanar. The housing and electromagnet structures are placed in abutting relation on opposite surface portions of the plate 90, and the assembly is secured together by a weld joining the respective adjacent outer surfaces of band 94 and housing section 38. As shown in FIG. 2, the axial end face of spool 82 contacts the central portion of plate 90 in a manner supporting the same, and the annular region between the end face of coil 84 and plate 90 is filled with a resinous encapsulant material 96.

By way of example, in an illustrative pump, spool 82, magnet housing 86 and washers 88 are of ferromagnetic material, for example 4750 nickel iron alloy. Plate 90 and band 94 are of titanium, the material of plate 90 being found suitable for use in the exemplary implanted drug delivery pump previously mentioned. Spool 82 has a length of about 0.555 inch and a diameter of 0.079 inch. Housing 86 has a wall thickness of about 0.03 inch, band 94 a thickness of about 0.02 inch and diaphragm 90 a thickness of about 0.001 inch. Coil 84 has about 3600 turns of 42 gauge wire.

The pump of the present invention further comprises a body 100 of magnetically permeable material in the fluid containing region of housing 12 and between the first and second fluid chambers 16 and 18, respectively. In addition to providing separation between the two chambers, body 100 also defines a portion of the magnetic circuit in the pump, along with other components of the pump, in a manner which will be described. Body 100 is generally solid cylindrical in shape having an outer diameter substantially equal to the diameter of the inner surface 40 of housing section 38 thereby providing a close fitting relationship. Body 100 has a main body portion between axial end surfaces 102 and 104 which is of an axial length less than the distance between housing surface 42 and plate 90 by an amount determined by the desired dimension of fluid chamber 18. Body 100 is formed to include an outer annular rim portion 106 extending from end face 102 and which abuts a corresponding surface portion of plate 90 as shown in FIG. 2. The radial thickness of rim portion 106 is substantially equal to that of magnet housing 86, and the two are in substantial alignment for maximizing transmission of magnetic flux therebetween in a manner which will be described.

Figure 1:
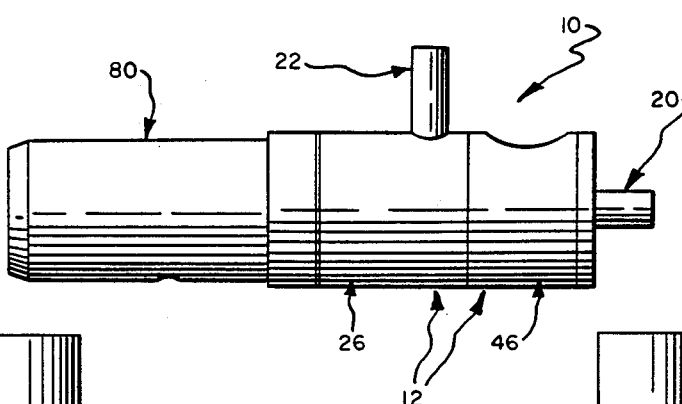
FIG. 1 is a side elevational view of a pump according to the present invention.
Figure 6:
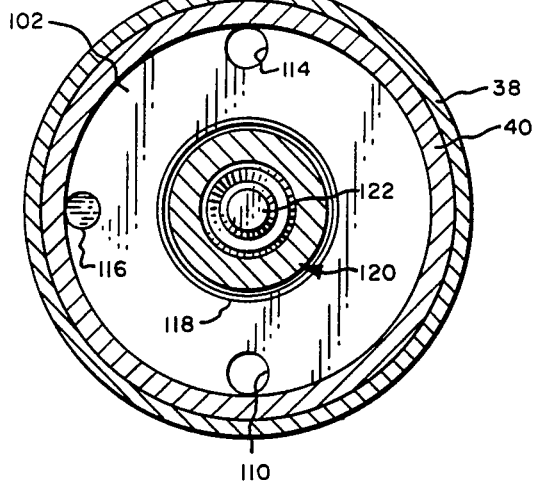
FIG. 6 is a sectional view taken about on line 6—6 in FIG. 2.
Figure 7:
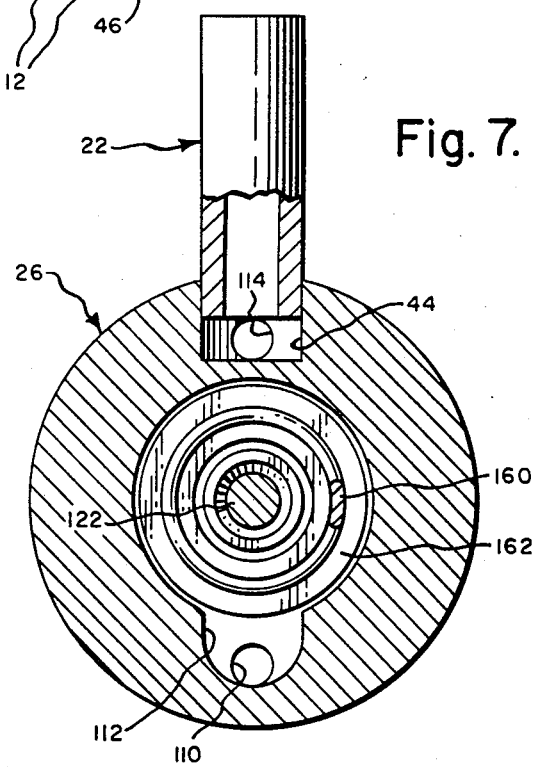
FIG. 7 is a sectional view taken about on line 7—7 in FIG. 2.
Figure 8:
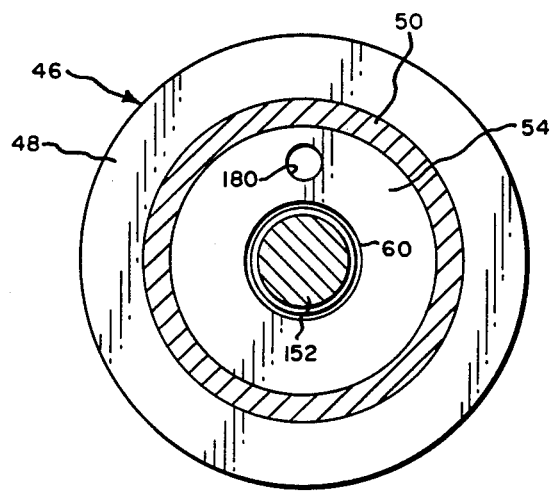
FIG. 8 is a sectional view taken about on line 8—8 in FIG. 2.
Figure 9:
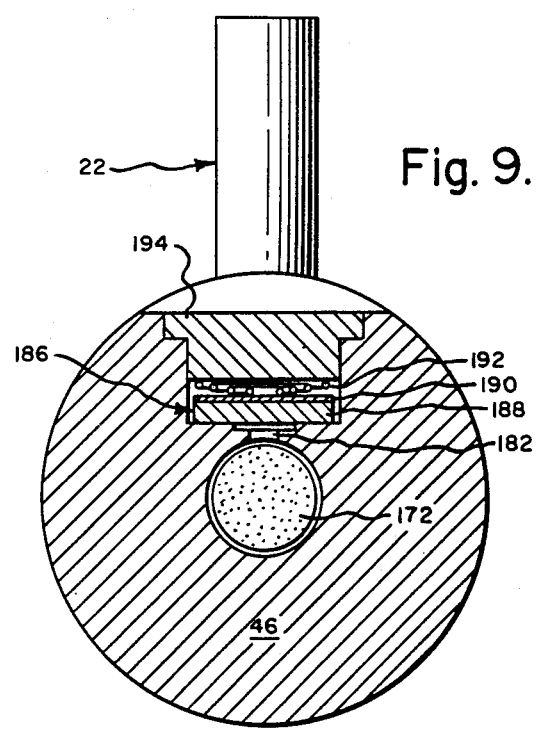
FIG. 9 is a sectional view taken about on line 9—9 in FIG. 2.

Body 100 is provided with a central through bore or passage 108 of substantial diameter of receiving a portion of the pump armature in a manner which will be described. In accordance with the present invention, body 100 also is provided with a through bore or passage 110 radially offset from passage 108 and in direct communication with the first and second fluid chambers 16 and 18, respectively, to allow bubbles in the fluid to bypass the body 100 and a portion of the pump armature in a manner which will be described. Bypass passage 110 has a longitudinal axis disposed parallel to the longitudinal axis of passage 108 and has a diameter less than that of passage 108. Bypass passage 110 extends from end face 102 of body 100 along the entire axial length of the body to end face 104. The end of passage 110 adjacent end face 102 opens directly to fluid chamber 18, and the end of passage 110 adjacent end face 104 opens through a recess 112 in a pump body 26 to pumping chamber 16. Body 100 is provided with another smaller diameter through bore or passage 114 offset from passage 108 in registry with outlet passage 44 and of substantially the same diameter as passage 44 for providing fluid communication between fluid chamber 18 and outlet 22. Body 100 is positioned in housing 12 by means of a rod 116 shown in FIG. 6 extending through corresponding bores in body 100 and valve housing portion 26, and rod 116 preferably being of Teflon material and the parts being secured together by a compression fit. The exterior surface of body 100 is coated with parylene material for corrosion resistance, and for convenience in illustration only the surface of central passage 108 is shown with the parylene coating 118.

By way of illustration, in an illustrative pump, body 100 is of mu-metal which is selected to provide the desired degree of magnetic permeability while at the same time being compatible with medicine or the like for use in the exemplary implanted drug delivery pump previously mentioned. As is well known, mu metal includes nickel in a major proportion with the balance including iron, copper and chromium. The outer diameter of body 100 is about 0.26 inch, the axial length between end face 104 and the end face of rim 106 is about 0.130 inch, and the axial length between end faces 102 and 104 is about 0.1 inch. Central passage 108 has a diameter of about 0.1 inch, bypass passage 110 has a diameter of about 0.029 inch and passage 114 has a diameter of about 0.029 inch.

The pump according to the present invention further comprises an armature generally designated 120 positioned in the fluid containing region of housing 12. The armature has a pole portion located for magnetic attraction by the electromagnet. The armature has a piston portion associated with the fluid receives chamber 14 for putting fluid from chamber 14 into chamber 18. The armature has the pole portion associated with fluid chamber 18 for movement within chamber 18 as shown in FIGS. 2-5. The armature is movably supported in housing 12 for movement from a rest position through a forward pumping stroke when attracted by the electromagnet 80 to force fluid out of the fluid chambers 16 and 18 through outlet 22, and for movement in an opposite direction through a return stroke back to the rest position. In FIG. 2, armature 120 is shown in a rest position prior to energization of electromagnet 80, in FIG. 3 armature 120 is shown during the forward pumping stroke in response to energization of electromagnet 80, in FIG. 5 armature 120 is shown at the end of the forward pumping stroke, and in FIG. 4 armature 120 is shown during the return to the rest position.

Armature 120 includes a shaft or rod portion 122 which is positioned in housing 12 with the longitudinal axis thereof generally coincident with the longitudinal axis of housing 12. Shaft portion 122 is of relatively small diameter. The armature further includes an enlarged body portion 124 of magnetically permeable material which provides the armature pole portion. Body 124 is solid cylindrical in shape having an outer diameter slightly smaller than the diameter of passage 108 in body 100. This is to allow reciprocal movement of armature body 124 within the body 100 during the forward and return strokes of armature 120. The armature body 124 terminates at the end facing electromagnet 80 in an axial end face 126 which serves as the pole face and is disposed substantially perpendicular to the armature axis. The pole face 126 together with electromagnet 80 define the magnetic circuit gap which is closed during the forward pumping stroke. The pole face 126 is of relatively large cross-sectional area as compared to the cross-sectional area of the armature shaft portion 122.

Shaft portion 122 is fixed to body 124 in the following manner. Body 124 is provided with a longitudinal bore 128 extending inwardly from the opposite axial end face 130 thereof which bore terminates within body 124 at a location spaced from pole face 126. A sleeve-like bushing 132 of fluoropolymer material such as Teflon is fitted in the bore, in particular a relatively thin-walled section of bushing 132 extends into bore 128 and a relatively thicker-walled section of bushing 132 extends axially outwardly from end face 130. The end of the armature shaft portion 122 is fixed in the outwardly extending section of the sleeve or bushing 132. The foregoing is provided by a mechanical compression fit.

Armature 120 includes another body portion generally designated 134 spaced axially from body 124, preferably integral with shaft portion 122, and of relatively larger diameter. Body portion 123 is located in pumping chamber 16 and provides an armature plunger portion in a manner which will be described. Body portion 134 has a first section 136 axially adjacent shaft portion 122 and having axial end face 138 facing armature body 124. Body portion 134 has a second section 140 axially adjacent section 136, of larger diameter, having a first axial end face 142 disposed toward armature body 124 and a second axial end face 144 disposed in the opposite direction. End face 142 together with the outer surface of section 126 define an annular shoulder facing in an axial direction toward the armature body 124 for a purpose to be described.

Armature 120 includes a piston portion generally designated 150 movably positioned within passage 60 of housing extension 46 and extending axially from body portion 134 toward inlet 20. Piston 150 is substantially cylindrical in shape having a first section 152 axially adjacent body 124 of slightly smaller diameter for a purpose to be described and a second section 154 of larger diameter. Section 154 also is of greater axial length as compared to section 152. The outer diameter of section 154 is slightly less than the diameter of passge 60 to allow reciprocal movement of piston 150 within housing extension 46 during the forward and return strokes of armature 120. Section 154 terminates in an axial end face 156 which faces toward inlet 20 and which includes a central extension 158 of relatively small diameter and axial length for a purpose to be described.

There is provided an armature biasing means in the form of a coil spring 160 for urging armature 120 toward the rest postibn shown in FIG. 2. One end of spring 160 seats in the annular shoulder described above and defined by end face 142 and the outer surface of section 136. The opposite end of spring 160 seats in an annular spring retainer element 162 which has an annular rim portion which abuts against the end face 104 of body 100 as shown in FIG. 2. The annular shape of retainer 162, with the two diameter rim sections, enables it to be located concentric with the armature shaft section 122 to receive the spring 160 which also is concentric with the shaft, while at the same time not interfering with body 124 during movement of the armature 120. The outer diameter of the largest rim portion of retainer 162 is substantially equal to the diameter of surface 26, and retainer 162 is merely located within the housing 12, being held in place by the force of spring 160.

By way of example, in an illustrative pump, the armature 120 including shaft portion 122, body portion 134 and piston portion 150 is machined from metal, preferably titanium for use in the aforementioned illustrative implanted drug delivery pump. The armature body or pole portion 124 is of mu-metal and retainer 162 is of titanium. In addition, the armature can be coated or plated with gold or other suitable material selected to enhance the compatibility of the drug with the armature external surface. The combination of armature shaft portion 122, body 134 and piston 150 has an overall length of about 0.260 inch from the end fitted within body 124 to the outer end of extension 158. The armature shaft portion 122 has an outer diameter of about 0.036 inch, section 136 has an outer diameter of about 0.093 inch and an axial length of about 0.020 inch, section 140 has an outer diamter of about 0.116 inch, and an axial length of about 0.015 inch, piston section 154 has an outer diameter of about 0.070 inch, and an axial length of about 0.060 inch, piston section 152 has an outer diameter of about 0.062 inch and an axial length of about 0.040 inch, and extension 158 has an outer diameter of about 0.020 inch and an axial length of about 0.005 inch. Body 124 has an overall axial length of about 0.14 inch and an outer diameter of about 0.1 inch. Spring 160 is 0.005 titanium wire with the spring inner diameter being about 0.095 inch.

The pump according to the present invention further includes a main check valve operatively coupled to the armature and located in the fluid-receiving region of the housing for opening and closing the pump inlet. In particular, the check valve comprises a valve member movably carried by the armature and positioned and biased for closing the pump inlet when the armature is in the rest position and allowing opening of the inlet after the armature begins movement associated with the forward pumping stroke. As shown in FIG. 2, the check valve, generally designated 170, is located in the fluid-receiving chamber 14 between inlet 20 and the armature piston end face 154. Check valve 170 includes a body or seat 172 in the form of a disc having a surface facing and adapted to sealingly contact the edge defined between surfaces 64 and 78 of the inlet fitting, a backing element 174 in the form of a thinner disc or squared circular element contacting the opposite surface of body 172, and a biasing spring 176 in the form of a conical spring between backing element 174 and piston end face 154. The valve seat 172 is loosely positioned in passage 60 and is relatively thin. As a result, seat swelling caused by temperature changes or the presence of various liquids has a smaller effect on the liquid volume delivered per stroke. This seat structure makes it possible to reduce the clearance between seat 172 and passage 60. The smaller clearance and thinner seat 172 together contribute significantly to reducing the volume of the fluid-receiving chamber 14 with armature 120 in the rest position. The backing element 174 provides a bearing surface for spring 176 at all times and for the projection 158 when armature 120 is at rest. The biasing spring 176 is compressed to an approximately flat configuration as shown in FIG. 2 when armature 120 is in the rest position.

The use of a conical spring permits another significant reduction in the volume of the fluid-receiving chamber 14 when armature 120 is at rest. With a conical spring, it is not necessary to allow for tolerances in spring shape when designing the cavity containing the spring. This avoids the situation of the practical volume of the spring cavity being larger than the minimum one required to contain the spring. With conical spring 176 these tolerances are eliminated and the spring cavity volume is decreased. Thus, the arrangement and structure of the check valve member and the provision of the conical spring minimizes the internal volume of the pump thereby limiting the maximum size of a bubble which can be contained therein.

By way of example, in an illustrative pump, the check valve body or seat 172 is a disc of #90125-1-2 elastomer medical grade silicone rubber having a diameter of about 0.064 inch and a thickness of about 0.015 inch. Backing element 174 is a squared disc of titanium 75A sheet having a circular diameter of about 0.066 inch, a length of about 0.055 inch between flats and a thickness of about 0.002 inch. Conical spring 176 is wound of 0.004 inch diameter GA1-4V titanium alloy wire to include four coils and to have a free length of about 0.038 inch, a force of about 2.0 grams at 0.002 above full compression, an outer diameter of about 0.095 inch and an inner diameter of about 0.050 inch.

The pump of the present invention further comprises a bypass passage in the pump body between the first pumping chamber 16 and the fluid receiving chamber 14 to provide a path for bubbles around the armature piston, which is closely movably fitted within the pump body, and check valve means in the bypass passage which opens during the return stroke of the armature 120. The need for the bypass path arises from the small clearance between piston section 154 and passage 60 requiring a potentially high pressure difference to force bubbles therethrough and the possiblity of a bubble becomming trapped between piston section 154 and passage 60 and preventing return of armature 120. In particular, housing extension 46 is provided with a longitudinally extending bore or passage 180 radially offset from passage 60 extending axially inwardly from end face 54 a distance beyond the center of body 46. A radially extending bore or passage 182 places passage 180 in communication with passage 60 at a location substantially mid-way between end faces 54 and 58 of extension 46. The junction of passages 180 and 182 includes a valve seat surface 184 formed in body 46. A check valve generally designated 186 normally blocks communication between passages 180 and 182. Check valve 186 includes a disc-shaped body or seat 188 having one surface contacting surface 184, a disc-shaped backing element 190 contacting the opposite surface of body 188, and a conical biasing spring 192 between backing element 190 and a plug 194 fitted in body 46.

If the pressure difference required to force a bubble between piston section 154 and passage 60 exceeds approximately 2.3 psi in a pump having the foregoing illustrative dimensions and return spring forces, the return of armature 120 may be prevented by a trapped bubble. Depending upon the surface properties of piston section 154 and passage 60, water at surface tension equal to 73 dynes/cm. is capable of preventing bubble flow with a clearance as large as 0.00037 inch on the radius. This is comparable to the actual clearance between piston section 154 and passage 60. Even if the bubble pressure is less than this value, the pressure in the pump chamber with the armature 120 at rest may exceed the pressure at pump outlet 22 and decreases the ability of the pump to operate against a pressure head.

The bypass check valve 186 provides a different path for bubbles past the armature piston portion 150. It is designed to open at a pressure head well below the pressure generated by the armature return spring 160. Preferably, the opening pressure for check valve 186 is also lower than the bubble point of the gap between piston section 154 and passage 60. The provision of bypass check valve 186 causes a rapid return stroke of armature 120, since the armature return no longer is limited by the rate of fluid leakage between armature piston 150 and passage 60. Instead the major part of the fluid moves from chamber 16 along passage 180 through check valve 186 and passage 182 into chamber 14 along with any bubbles contained in the fluid.

The provision of bypass check valve 186 as an alternate bubble path offers two principal advantages. First, it reduces the dependence of the pump behavior with bubbles present upon the fluid surface tension, the surface properties of armature piston 150 and passage 60, and the clearance between piston 150 and passage 60. Second, and perhaps more important, it preserves the continuity of the water film between piston 150 and passage 60 during bubble passage. Since this water film plays important role in operation of the pump, it is important that it not be weakened by the presence of a bubble spanning part of its length.

By way of example, in an illustrative pump, passage 180 has a diameter of about 0.020 inch, passage 182 has a diameter of about 0.0145 inch, and valve seat surface 184 has a diameter of about 0.093 inch. The distance between surface 184 and the surface of plug 194 is about 0.054 inch. Check valve body 188 is of the same material as check valve body 172 and has a diameter of about 0.089 inch and a thickness of about 0.002 inch. Backing element 190 is a disc of #90119-2 titanium 74 A sheet having a diameter of about 0.090 inch and a thickness of 0.002 inch. Conical spring 192 is wound of 0.004 inch diameter 6A1-4V titanium alloy wire to include four coils and to have a free length of about 0.002 inch, a force of about 1.0 grams at 0.002 above full compression, an outer diameter of about 0.095 inch and an inner diameter of about 0.050 inch.

In operation, inlet 20 is connected to a source or supply of fluid to be pumped, and outlet 22 is connected to a point or location of use for the pumped fluid. The armature 120 is moved through a forward pumping stroke in response to electrical energization of electromagnet 80. One way of energizing magnet 80 is to charge a capacitor from a battery and then discharge that capacitor through coil 84. Other procedures can of course be employed for electrically energizing coil 84 in a known manner. Prior to electrical energization of magnet 80, armature 120 is in the rest position illustrated in FIG. 2 where the check valve 170 is located with surface of body 172 seated against the edge between surfaces 64,78 surrounding the opening of the inlet fitting passage to block fluid communication from inlet 20 to the fluid receiving chamber 14. In the rest position of armature 120, pole face 126 is spaced from diaphragm 90 as shown in FIG. 2 thereby defining the gap in the magnetic circuit. In the rest position, this gap between pole face 126 and diaphragm 90 is of maximum length. When coil 84 is electrically energized, the armature pole portion 124 is attracted toward magnet 80 thereby causing armature 120 to be drawn toward diaphragm 90. Electromagnetic flux travels through the magnetic circuit including the electromagnet core 82, washers 88, magnet housing 86, rim 106 of body 100, the included portion of diaphragm 90 between housing 86 and rim 106, body 100, armature pole portion 124, and the gap between pole face 126 and diaphragm 90. As armature 120 is moved in the forward pumping stroke, i.e. in a direction to the left as viewed in FIGS. 2–5, fluid initially contained in the passage 60 in housing portion 46, which is in communication with fluid receiving chamber 14, is forced by piston 150 through chamber 16, which may be viewed as a central, fluid transmitting chamber, through recess 112 and bypass passage 110 into the second fluid chamber 18. In this connection, plunger 134 may be viewed as an extension of piston 150. Any bubble contained in the fluid will take this path. Simultaneously, fluid contained in the second fluid chamber 18, i.e. the region between body 100, diaphragm 90 and pole portion 124, is thereby forced out through passages 114 and 44 and out through the outlet 22.

The bypass channel or passage 110 leads the flow through solenoid ring or body 100 for the purpose of permitting bubbles to pass the armature pole portion 124 and solenoid ring 100 with little pressure drop.

Without bypass passage 110, it would be necessary for the bubble to pass through the small gap or clearance between armature pole portion 124 and passage 108 in body 100 which would require a significant pressure drop, the magnitude depending upon the size of the clearance gap, the surface condition of the parts, and the surface tension of the fluid. Therefore, without bypass passage 110 bubbles normally would be trapped within the pump body. The provision of bypass passage 110 removes any requirement that armature pole portion 124 and armature piston 150 be of the same diameter. As a result, the armature piston 150 can be of relatively smaller diameter for accurate pumping at smaller volumes per pulse.

The check valve 170 moves freely with respect to the armature 120 and does not necessarily move when the armature 120 is drawn toward diaphragm 90. Such relative positions are illustrated, for example, in FIGS. 3 and 5. At rest, the surface of check valve body 172 is held in contact with the end of the inlet fitting by the spring 160 acting upon the armature 120 which is then in contact with check valve body 172 through element 174 and the compressed spring 176 as shown in FIG. 2. When the armature 120 is drawn toward diaphragm 90, the force of spring 160 is no longer transferred to the check valve 170 and the force holding the surface of check valve body 172 against the inlet fitting is decreased to that provided by spring 176, which generally provides a force less than that provided by spring 160. If armature 120 is drawn toward electromagnet 80 with sufficient velocity, pressure within the pump housing 12 between the end face 156 of piston 150 and the check valve body 172 decreases to a level below the level at the pump inlet 20, and the net force due to fluid pressure from inlet 20 acting on the check valve 170 tends to move the surface of check valve body 172 away from contact with the end of the inlet fitting. If the net force due to the fluid pressure exceeds that provided by the spring 176, then check valve 170 moves away from the inlet fitting and fluid flows into the pump body. In fact, because the fluid is nearly incompressible the check valve 170 opens at approximately the same time that the armature 120 achieves enough velocity to force fluid out of the pump outlet 22. The forward pumping stroke of the armature 120 is completed when the pole face 126 approaches contact with the diaphragm 90. Actual contact may not be achieved since viscosity limits out flow of the fluid between the pole face 126 and the diaphragm 90. When the armature velocity decreases to a level such that the displacement rate of the motion of the pole portion 124 no longer exceeds the leak rate between the outer surface of armature piston section 154 and passage 60, the pressure within the pump housing 12 begins to increase. When the force due to the pressure difference across the check valve 170 no longer exceeds the force of spring 176, the check valve member moves toward the end of the inlet fitting and prevents flow out of the inlet port 20 of the pump.

Figure 4:
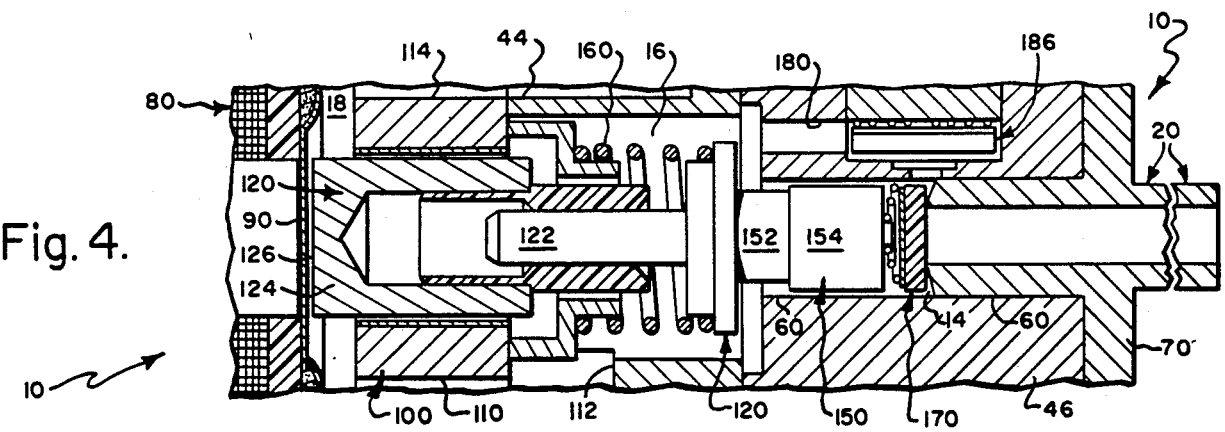
FIG. 4 is a fragmentary longitudinal sectional view of the pump of FIG. 2 showing the armature in a return position with the check valve in a closed position and the bypass check valve in an open position.
Figure 5:
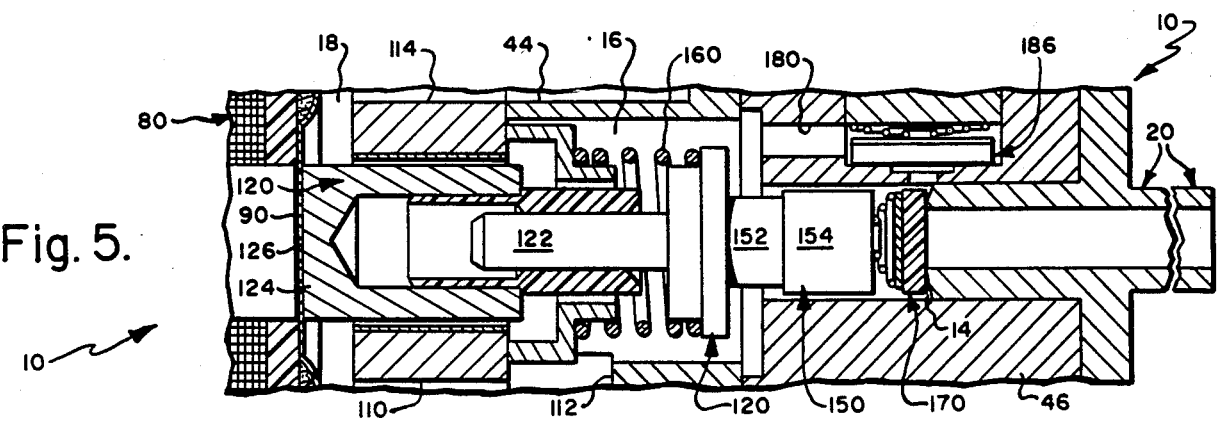
FIG. 5 is a fragmentary longitudinal sectional view of the pump of FIG. 2 showing the armature in an energized position with the main check valve in a closed position and the bypass check valve in a closed position.

When electrical excitation of coil 84 ceases, armature 120 is moved in the opposite direction, i.e. to the right as viewed in FIGS. 2–5, by the force of biasing spring 160 until the armature reaches the rest position as shown in FIG. 2. During the return stroke the bypass check valve 186 is open as shown in FIG. 4 with the result that the motion of armature 120 is relatively rapid as previously described. During the return stroke of armature 120 the check valve 170 is held against the inlet fitting primarily by the light spring 176 supplemented by the outlet and inlet pressures acting on the valve seat. When the return stroke is completed the spring force is increased to that of spring 160. The average pumping rate is determined by the rate of return of armature 120 to the rest position. Thus, the relatively rapid return of armature 20 provided by bypass check valve 186 increases the maximum available pumping rate. Armature 120 remains in the rest position of FIG. 2 with inlet 20 closed and waiting for the next forward pumping stroke which occurs when magnet 80 is engerized again.

Long term sealing is provided by the relatively stronger spring 160, and short term sealing while armature 120 is forward is provided by the relatively weaker spring 176. As a result, there can be satisfactory sealing against the back flow when the pump is not in operation, while the pressure drop across the check valve 170 during the pump stroke is small.

As previously described, the provision of bypass passage 110 around armature pole portion 124 and through body 100 avoids any requirement that armature pole portion 124 and armature piston 150 be of the same diameter and, as a result, enables armature piston 150 to be of relatively smaller diameter in the pump shown. The reduction in the diameter of armature piston 150 allows it to pump against higher back pressures without saturating the existing magnetic circuit. An additional advantage of this configuration is that for a given stroke volume, the smaller diameter of piston 150 allows that the linear stroke be longer. This tends to improve the stability of the stroke volume since the effect of seat swelling or stroke volume is smaller. Another advantage arises from the fact that the volume of the pump chamber 14 with armature 120 in the rest position is smaller for the smaller combination of piston 150 and passage 60.

The smaller diameter section 152 of piston 150 provides a necking down of the piston at its downstream end for the purpose of reducing the tendency of a bubble to be drawn back into the clearance between armature piston 150 and passage 60. As previously mentioned, continuity of the liquid film in this clearance is important to operation of pump 10. The film maintains the required pressure dop on opposite sides of piston 150 during the pumping stroke, and a gas bubble in that clearance could provide a leak thereby tending to equalize pressure on opposite sides of piston 150. The necked down section 152 of piston 150 provides a route by which liquid may move around a bubble in the space between section 152 and passage 60 and thereby move into and along the gap between piston section 154 and passage 60.

The pump 10 according to the present invention thus has the capability of operating with bubbles in the inlet fluid stream. By decreasing the volume of the pump chamber 14 to limit the maximum size of the bubble which can be contained within it, by providing the bypass path 110 through body 100 and around piston pole portion 124, by providing an alternate flow around armature piston 150 through passage 180 and 182C and check valve 186, a pump according to the present invention built according to the foregoing illustrative specifications has been found to continue to pump water against a pressure of 10 psi even when challenged by bubbles as large as 10 microliters in volume. In addition, the provisions enabling operation with bubbles also have provided an increase in the maximum available pumping rate and some relaxation of tolerance in the fit of the armature piston 150 in the pump body.

By way of further illustration, a pump according to the present invention having the foregoing illustrative dimensions has a pump chamber 14 volume of slightly less than 0.6 microliter when armature 120 is in a rest postion. With the pump pumping water against a 5 psi head at 3 seconds per energizing pulse, a sequence of air bubbles of volumes of 1, 3, 5, 7 and 10 microliters each were introduced to tubing connected to inlet 20. In each case the volume of fluid pumped per energizing pulse decreased from the bubble-free value of about 0.42 microliters to approximately 0.21–0.30 microliters per pulse. The pump then recovered in approximately one hour to pump at the bubble-free rate of about 0.42 microliters per pulse. These bubble volumes are larger than the pump chamber volume and much of the bubble volume apparently passed beyond piston 150 immediately. Presumably the bubble volume which remained then dissolved gradually in the flowing water.

By way of further example, a pump according to the present invention was operated against a back pressure of 3 psi. with a bubble volume of 3 microliters and at pump frequencies of 16 seconds per pulse and 2 seconds per pulse. The volume per pulse recovered to the bubble-free rate of about 0.4 microliter in about 40 minutes at the higher pulse frequency and in about 3 hours at the lower rate. The volume of water passed by the pump in those time periods would have been sufficient to dissolve 0.9 microliters of nitrogen at the lower frequency and 1.7 microliters at the higher frequency if it is assumed that the inlet water was saturated with dissolved nitrogen. It is reasonable to assume that at the lower pulse rate the flowing water reaches saturation in the pump chamber 14 but at the higher rate it does not. Based on that assumption, the total water flow required for pump recovery at the lower pulse rate can be used to determine the approximate initial size of the bubble in the pump chamber 14, in this case 0.9 microliters which corresponds approximately to the full volume of the pump chamber 14.

Thus pump 10 accordingly has the capability of operating with bubbles in the inlet liquid stream. Pump 10 also has the advantage of operating at extremely low power levels, being compatible with drugs and similar liquids to be pumped, being electrically and magnetically efficient, and being small in size, light in weight and reliable in operation. In particular, the non-movable diaphragm 90 of titanium or like material provides an hermetic seal between the fluid in housing 12 and the electrical components associated with magnet 80. Having armature 120 immersed in the fluid makes operation of the pump nearly independent of ambient pressure. The initial condition of the pump when armature 120 is in the rest position of FIG. 2 is that the fluid is at substantially the same pressure on opposite sides of the pump piston, i.e. in the receiving chamber 14 and in the pumping chambers 16 and 18.

The pump of the present invention is made electrically and magnetically efficient by minimizing the total gap within the magnetic circuit, by having the magnetic pole face 126 of relatively large surface area, and by having core 82 of relatively small diameter. In particular, there is a relatively large contact area at the interface between the axial end face of magnet housing 86 and diaphragm 90 and between diaphragm 90 and the axial end face of rim 106 of body 100 to minimize the effective air gap introduced by diaphragm 90 at this point in the magnetic circuit. Related to this is the need for welding diaphragm 90 to the band 94 and housing section 38 to achieve an hermetic seal between electromagnet 80 and the fluid containing region of housing 12 while at the same time not adversely affecting the magnetic circuit. In addition, there is a relatively large surface area along the gap between body 100 and pole portion 124 to minimize the effective air gap introduced at this point in the magnetic circuit. The relatively small diameter of core 82 provides the necessary ampere turns with a minimum electrical resistance. The large area of pole face 126 provides a high magnetic force with a minimum number of ampere turns. Having the magnetic gap external to coil 84, i.e. between ple face 126 and diaphragm 90, allows the foregoing features to be achieved simultaneously.

It is therefore apparent that the present invention accomplishes its intended objects. While an embodiment of the present invention has been described in detail, this is for the purpose of illustration, not limitation.

We claim:

1. An electromagnetic pump comprising:
  (a) an elongated housing having a longitudinal axis and having an interior fluid containing region including a fluid receiving chamber and a fluid pumping chamber in fluid communication therewith, an inlet in fluid communication with said receiving chamber and an outlet in fluid communication with said pumping chamber;
  (b) check valve means operatively associated with said fluid containing region for allowing fluid flow in a direction from said inlet through said outlet and blocking fluid flow in a direction from said outlet through said inlet;
  (c) electromagnet means carried by said housing and located external to said fluid containing region;
  (d) an armature positioned in said fluid containing region of said housing for movement along said housing longitudinal axis and having a pole portion located for magnetic attraction by said electromagnet means and having a piston portion operatively associated with said fluid receiving and pumping chambers for forcing fluid from said receiving chamber through said outlet; said armature being movably supported in said housing for movement from a rest position through a forward pumping stroke when attracted by said electromagnet means to force fluid from said receiving chamber through said outlet and for movement in an opposite direction through a return stroke back to said rest position;
  (e) means defining a magnetic circuit including said electromagnet means and said armature and a gap between said pole portion of said armature and said electromagnet means for moving said armature toward said electromagnet means to close said gap in response to electrical energization of said electromagnet means;
  (f) said check valve means comprising a thin body movably carried by said armature and located in said interior fluid containing region in small clearance relation therewith and between said armature and said inlet, and a conical spring between said valve body and said armature thereby enabling said pump chamber to have dimensions which define a volume not greater than about one and one-half times the stroke volume of the pump which therefore limits the volume of a bubble in the fluid which can be contained in said pump chamber up to a volume of about one and one-half times the stroke volume the pump when said armature is in a rest position so as to enable said pump to operate with bubbles present in the fluid being pumped;
  (g) said armature pole portion having a pole face located to define said gap with said electromagnet means; and
  (h) said fluid-containing region of said housing and said electromagnet means being in axially spaced relation along said housing longitudinal axis and being separated by barrier means of fluid impervious material having opposite sides, said fluid containing region, inlet, outlet and armature all being located on one side of said barrier means and said electromagnet means being located on the opposite side of said barrier means.

2. A pump according to claim 1, wherein said check valve means is operatively coupled to said armature and located in said fluid receiving chamber for opening and closing said inlet, said check valve means having a structure, size and relatively close clearance with said chamber so as to determine the volume of said fluid-receiving chamber and thereby limit the size of a bubble which can be contained in said chamber.

3. A pump according to claim 2, wherein said armature has an end face disposed in a plane substantially perpendicular to the direction of movement of said armature and located in said fluid-receiving chamber and facing said inlet, and wherein said check valve means is movably carried by said armature on said end face and comprises:
  (a) a valve body; and
  (b) biasing means between said valve body and said armature end face for moving said body into a position closing said inlet.

4. A pump according to claim: 3, wherein said valve body is of elastomer material in the form of a disc having a planar surface thereof facing said inlet for closing the same, said disc having a diameter selected to provide a relatively close, movable and loose fit in said fluid receiving chamber and said disc being relatively thin.

5. A pump according to claim 3, wherein said biasing means comprises a conical spring having one end operatively contacting said valve body and having the opposite end contacting said armature end face.

6. A pump according to claim 1, wherein said armature piston portion is located between a plunger portion and said pump inlet and movable within said pump housing, there being a relatively small clearance between said armature piston portion and said housing, said armature piston portion including two axially adjacent sections of different cross-section, one of said sections being axially near said plunger portion and of smaller cross-section than the other of said sections, the clearance between said one section and said housing being slightly larger than the clearance between said other section and said housing thereby serving to prevent entry of bubbles into the clearance between said other section and said housing.

7. A pump according to claim 1, wherein said armature pole portion has a pole face of relatively large area disposed in a plane substantially perpendicular to the direction of movement of said armature.

8. An electromagnetic pump comprising:
  (a) an elongated housing having a longitudinal axis and having an interior fluid containing region including a fluid receiving chamber, a first fluid chamber in fluid communication therewith, a second fluid chamber in fluid communication with said first fluid chamber, an inlet in fluid communication with said receiving chamber and an outlet in fluid communication with said second fluid chamber;

(b) electromagnet means carried by said housing and located external to said fluid containing region;

(c) an armature positioned in said fluid containing region of said housing for movement along said housing longituginal axis and having a pole portion located for magnetic attraction by said electromgnet means and having a piston portion operatively associated with said fluid receiving and said first fluid chambers for forcing fluid from said fluid receiving chamber through said first and second chambers and out through said outlet, said armature being movably supported in said housing for movement from a rest position through a forward pumping stroke when attracted by said electromagnet means to force fluid from said chambers through said outlet and for movement in an opposite direction through a return stroke back to said rest position;

(d) means for defining a magnetic circuit including said electromagnet means and said armature and a gap between said pole portion of said armature and said electromagnet means for moving said armature toward said electromagnet means to close said gap in response to electrical energization of said electromagnet means;

(e) check valve means operatively coupled to said armature and located in said fluid containing region of said housing for closing said inlet when said armature is in said rest position and for opening said inlet after said armature begins movement associated with said forward pumping stroke, said check valve means allowing fluid flow in a direction from said inlet through said outlet and blocking fluid flow in a direction from said outlet through said inlet;

(f) said armature piston portion being located between a plunger portion and said pump inlet and movable within said pump housing, there being a relatively small clearance between said armature piston portion and said housing, said armature piston portion including two axially adjacent sections of different cross-section, one of said sections being axially near said plunger portion and of smaller cross-section than the other of said sections, the clearance between said one section and said housing being slightly larger than the clearance between said other section and said housing and thereby serving to prevent entry of bubbles into the clearance between said other section and said housing;

(g) said armature pole portion having a pole face located to define said gap with said electromagnet means; and (h) said fluid-containing region of said housing and said electromagnet means being in axially spaced relation along said housing longitudinal axis and being separated by barrier means of fluid impervious material.

9. A pump according to claim 8, further including a body in said housing fluid containing region between said first and second fluid chamber, said body having a passage therethrough for receiving said armature pole portion in a movable, relatively close fitting relation and further including:
means for providing a bypass passage in said body in direct communication with said first and second fluid chambers to allow bubbles in the fluid to pass said body and said armature pole portion with little pressure drop.

10. A pump according to claim 9, wherein said armature piston portion is located between a plunger portion and said pump inlet, said piston portion having a cross-sectional size smaller than the cross-sectional size of said armature pole portion.

11. A pump according to claim 8, wherein said check valve means is located in said fluid receiving chamber for opening and closing said inlet, said check valve means having a structure, size and relatively close clearance with said chamber so as to determine the volume of said fluid-receiving chamber and thereby limit the maximum size of a bubble which can be contained in said chamber.

12. A pump according to claim 11, wherein said armature has an end face disposed in a plane substantially perpendicular to the direction of movement of said armature and located in said fluid-receiving chamber and facing said inlet, and wherein said check valve means is movably carried by said armature on said end face and comprises:

(a) a valve body; and
(b) biasing means between said valve body and said armature end face for moving said body into a position closing said inlet.

13. A pump according to claim 12, wherein said valve body is of elastomer material in the form of a relatively thin disc having a planar surface thereof facing said inlet for closing the same, said disc having a diameter selected to provide a relatively close, movable and loose fit in said fluid receiving chamber, and wherein said biasing means comprises a conical spring having one end operatively contacting said valve body and having the opposite end contacting said armature end face.

14. A pump according to claim 8, wherein said armature piston portion is located between a plunger portion and said pump inlet and movable within said housing, there being a relatively small clearance between said armature piston portion and said housing, and further including;
means for providing a bypass path for bubbles in the fluid around said armature piston portion between said first fluid chamber and said fluid receiving chamber.

15. A pump according to claim 14, wherein said path providing means comprises:
(a) passage means in said housing for placing said first fluid chamber and said fluid receiving chamber in fluid communication; and
(b) check valve means in said passage means normally closed during said forward pumping stroke of said armature and normally open during said return stroke of said armature.

16. A pump according to claim 8, said barrier means having opposite sides, said fluid containing region, inlet, outlet and armature all being located on one side of said barrier means and said electromagnet means being located on the opposite side of said barrier means.

17. A pump according to claim 8, wherein said armature pole portion has a pole face of relatively large area disposed in a plane substantially perpendicular to the direction of movement of said armature.

18. An electromagnetic pump comprising:
(a) a housing having an interior fluid containing region including a fluid receiving chamber and a fluid pumping chamber in fluid communication therewith, an inlet in fluid communication with said receiving chamber and an outlet in fluid communication with said pumping chamber;
(b) check valve means operatively associated with said fluid containing region for allowing fluid flow in a direction from said inlet through said outlet and blocking fluid flow in a direction from said outlet through said inlet;
(c) electromagnet means carried by said housing and located external to said fluid containing region;
(d) an armature positioned in said fluid containing region of said housing having a pole portion located for magnetic attraction by said electromagnet means and having a piston portion operatively associated with said fluid receiving and pumping chambers for forcing fluid from said receiving chamber though said outlet; said armature being movably supported in said housing for movement from a rest position through a forward pumping stroke when attracted by said electromagnet means to force fluid from said receiving chamber through said outlet and for movement in an opposite direction through a return stroke back to said rest position, said armature piston portion being located between a plunger portion and said pump inlet and movable within said housing, there being a relatively small clearance between said armature piston portion and said housing;
(e) means defining a magnetic circuit including said electromagnet means and said armature and a gap between said pole portion of said armature and said electromagnet meand for moving said armature toward said electromagnet means to close said gap in response to electrical energization of said electromagnet means; and
(f) controlled means for providing a bypass path for bubbles in the fluid around said armature piston portion between said fluid pumping chamber and said fluid receiving chamber only during said return stroke of said armature.

19. A pump according to claim 1, wherein said path providing means comprises:
(a) passage means in said housing for placing said fluid pumping chamber and said fluid receiving chamber in fluid communication; and
(b) check valve means in said passage means movably closed during said forward pumping stroke of said armature and normally open during said return stroke of said armature.

20. A pump according to claim 19, wherein said passage means comprises a first passage leading from said fluid pumping chamber in a direction generally parallel to the direction of movement of said armature, a second passage leading from said first passage to said fluid receiving chamber, and means defining a valve seat at the junction between said first and second passages, and wherein said check valve means comprises a valve body positioned for movement in said first passage and having a surface adapted to contact said valve seat and biasing means operatively contacting said valve body and a surface of said first passage, said biasing means normally urging said valve body into contact with said valve seat to block fluid communication between said first and second passages and operable to allow movement of said valve body away from said valve seat to place said first and second passages in fluid communication.

* * * * *

UNITED STATES PATENT AND TRADEMARK OFFICE
CERTIFICATE OF CORRECTION

PATENT NO. : 4,636,150

DATED : January 13, 1987

INVENTOR(S) : Theodore J. Falk et al

It is certified that error appears in the above-identified patent and that said Letters Patent are hereby corrected as shown below:

Claim 1, part f) on line 13 thereof insert --of-- before " the pump when ..."

Claim 4, line 1, delete ":" after claim

Claim 9, line 3, change "chamber" to --chambers--.

Claim 11, line 7 delete "maximum".

Signed and Sealed this

Twentieth Day of October, 1987

Attest:

DONALD J. QUIGG

Attesting Officer

Commissioner of Patents and Trademarks